US00PP20335P2

(12) United States Plant Patent
Ogilvy

(10) Patent No.: US PP20,335 P2
(45) Date of Patent: Sep. 22, 2009

(54) ***PHORMIUM* PLANT NAMED 'TAYA'**

(50) Latin Name: ***Phormium* hybrid**
Varietal Denomination: Taya

(76) Inventor: David Ogilvy, 208 Narrows Road, RD2 Hamilton (NZ)

( * ) Notice: Subject to any disclaimer, the term of this patent is extended or adjusted under 35 U.S.C. 154(b) by 0 days.

(21) Appl. No.: 12/217,925

(22) Filed: Jul. 10, 2008

(51) Int. Cl.
*A01H 5/00* (2006.01)

(52) U.S. Cl. ..... Plt./373

(58) Field of Classification Search ..... Plt./373
See application file for complete search history.

*Primary Examiner*—Kent L Bell
(74) *Attorney, Agent, or Firm*—Penny J. Aguirre

(57) ABSTRACT

A new cultivar of hybrid *Phormium* named 'Taya' that is characterized by its dark purple black foliage that is consistent throughout the leaf and its arching plant habit.

2 Drawing Sheets

Botanical classification: *Phormium* hybrid.
Cultivar designation: 'Taya'.

BACKGROUND OF THE INVENTION

The present invention relates to a new and distinct cultivar of *Phormium* of hybrid origin and referred to hereafter by its cultivar name, 'Taya'. The new cultivar is grown for use as a foliage plant for landscape and container use.

The Inventor discovered the new cultivar in his nursery in Hamilton, New Zealand in summer of 2004. The new cultivar was selected in a trial bed that was planted with seedlings that were derived from open pollination between *Phormium tenax* 'Purpurea' (not patented), unnamed selections of *Phormium cookianum* and unnamed selections of *Phormium tenax*. The Inventor was evaluating the seedlings for distinct foliage coloration. The exact parentage is unknown.

Asexual reproduction of the new cultivar was first accomplished by division in autumn of 2004 in Hamilton, New Zealand by the Inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Taya' as a new and unique cultivar of *Phormium*.

1. 'Taya' exhibits foliage that is deep purple black in color.
2. 'Taya' exhibits foliage coloration that is consistent throughout the leaf blade.
3. 'Taya' exhibits an arching plant habit.

In comparison to the *Phormium tenax* 'Purpurea', 'Taya' has darker purple black foliage with more consistent coloration throughout the leaf, and is more arching in habit.

*Phormium cookianum* has a similar in plant habit but the species has green foliage and known cultivars have variegated foliage.

The closest comparison plant is *Phormium tenax* 'Merlot' (U.S. Plant Pat. No. 14,228). 'Taya' differs from 'Merlot' in having darker colored foliage, in lacking a different colored margin, in being shorter in height with smaller, narrower leaves, and by exhibiting a more arching plant habit.

BRIEF DESCRIPTION OF THE DRAWING

The accompanying colored photographs illustrate the overall appearance and distinct characteristics of the new *Phormium*. The photographs in FIG. 1 and FIG. 2 were taken of a two year-old plant of 'Taya' as grown outdoors in a 2.5-liter container in Hamilton, New Zealand.

Figure 1:
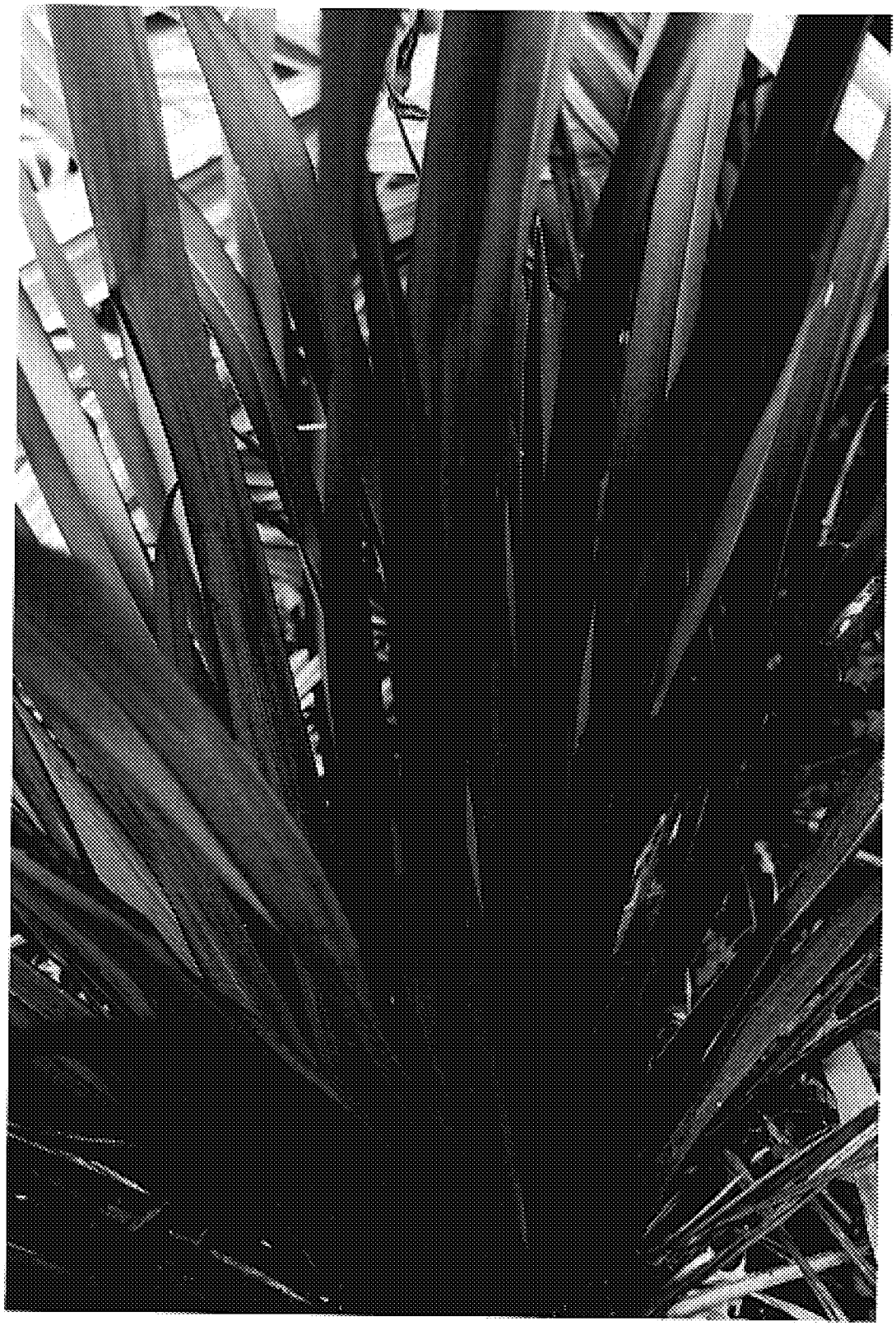
FIG. 1 provides a side view of 'Taya' and FIG. 2 provides a close up view of a leaf of 'Taya'.
Figure 2:
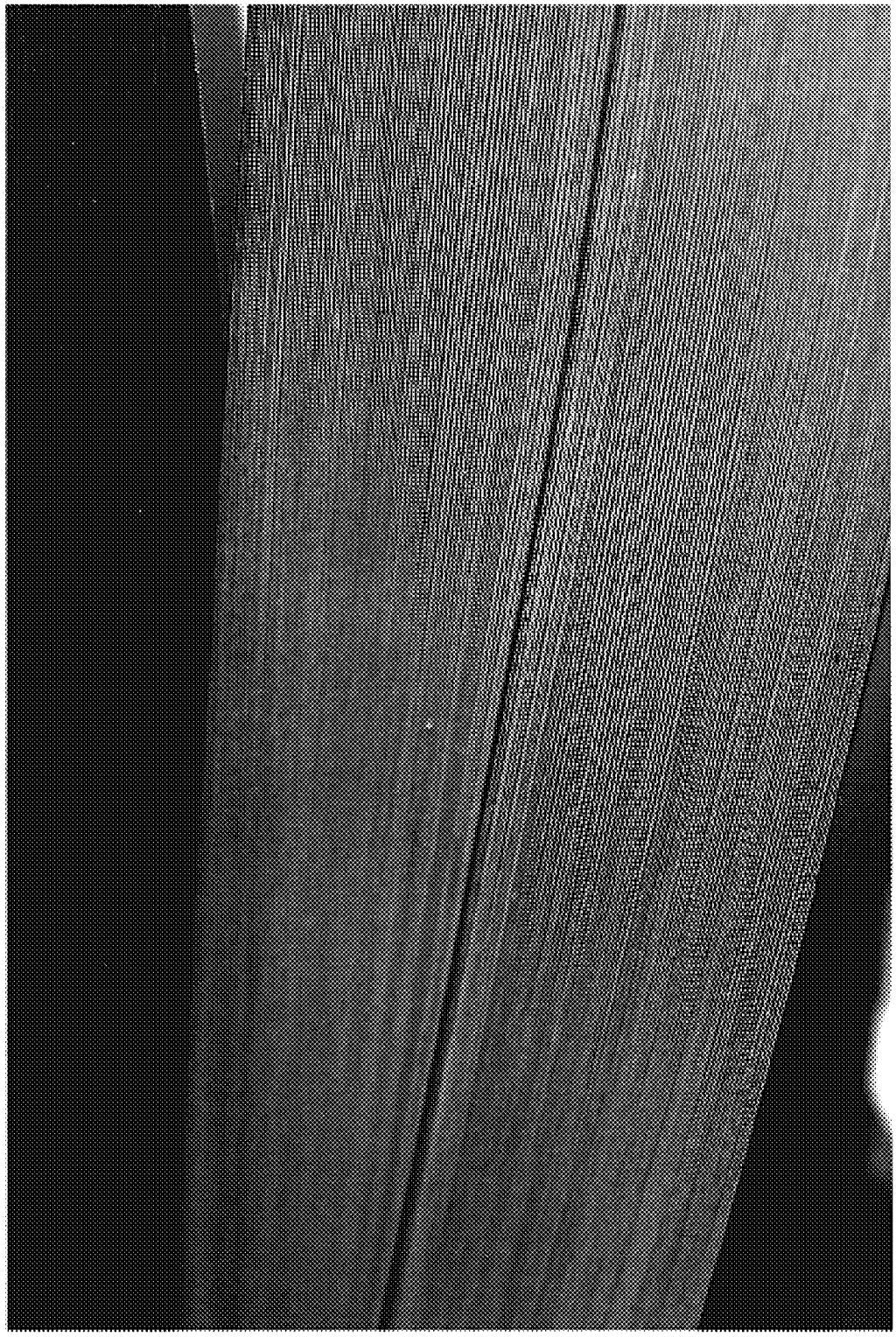

The colors in the photographs are as close as possible with the photographic and printing technology utilized. The color values cited in the detailed botanical description accurately describe the colors of the new *Phormium*.

DETAILED BOTANICAL DESCRIPTION OF THE PLANT

The following is a detailed description of two year-old plants of the new cultivar as grown outdoors in 2.5-liter containers in Hamilton, New Zealand. The plants were grown under average day temperatures of 18 to 24° C. and average night temperatures of 4 to 10° C. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Blooming period.*—No flower production has been observed.

*Plant type.*—Perennial.

*Plant habit.*—Clump-forming, emerge upright and become arching.

*Height and spread.*—Reaches about 80 cm in height and 60 cm in width when in the landscape.

*Hardiness.*—U.S.D.A. Zones 9a to 10b, tolerant to high temperatures of 35° C. and low temperatures of −5° C.

*Diseases and pests.*—No unique susceptibility or resistance to diseases or pests has been observed.

*Root description.*—Fibrous and fleshy roots that develop strongly into fibrous mat, 163B in color.

*Propagation.*—Division.

*Growth rate.*—Moderate, vigor typical to other cultivars of *Phormium.*

*Root development.*—Divisions establish in a 1 liter container is 8 to 12 weeks and fully develop a 2.5 liter container in 6 months from a 1 liter tranplant.

*Stem description.*—Stem-less, leaves are equitant from base.

Foliage description:

*Leaf shape.*—Lanceolate.

*Leaf division.*—Simple.

*Leaf base.*—Sheathed at base of leaf, sheath is 163C in color, bottom section of leaf is sulcate in shape (occasionally closed) then flattens to blade.

*Leaf apex.*—Acuminate.

*Leaf venation.*—Parallel, not prominent, same color as leaves.

*Leaf margins.*—Entire.

*Leaf attachment.*—Sheathed, lacks petioles.

*Leaf arrangement.*—Equitant.

*Leaf number.*—Average of 10 to 20 in a 2.5 liter container.

*Leaf orientation.*—Held upright and becomes arching.

*Leaf substance.*—Thick, stiff, leathery, durable.

*Leaf surface.*—Smooth, upper surface shiny, lower surface dull.

*Leaf color.*—Young leaves upper surface; N186A, young leaves lower surface; N186A with pruinose coating of 198A, mature leaves upper surface; N187A, mature leaves lower surface; N186A with pruinose coating of 198A.

*Venation.*—Parallel, same color as leaf.

*Leaf size.*—Average of 43 cm in length and 2.5 cm in width in a 2.5 liter container.

It is claimed:

1. A new and distinct cultivar of *Phormium* plant named 'Taya' as herein illustrated and described.

* * * * *